(12) United States Patent
Thorslund et al.

(10) Patent No.: US 8,387,803 B2
(45) Date of Patent: Mar. 5, 2013

(54) PARTICLE SORTING

(75) Inventors: Sara Thorslund, Uppsala (SE); Linda Johansson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 1134 days.

(21) Appl. No.: 12/198,642

(22) Filed: Aug. 26, 2008

(65) Prior Publication Data

US 2012/0160746 A1 Jun. 28, 2012

(51) Int. Cl.
*B07C 5/00* (2006.01)

(52) U.S. Cl. .................. 209/552; 209/906; 210/748.02; 210/748.05

(58) Field of Classification Search .................. 209/552, 209/590, 932; 210/748, 748.02, 748.05; 73/587
See application file for complete search history.

(56) References Cited

U.S. PATENT DOCUMENTS

| | | | | |
|---|---|---|---|---|
| 3,984,307 A * | 10/1976 | Kamentsky et al. | .......... | 209/546 |
| 4,759,775 A * | 7/1988 | Peterson et al. | .............. | 210/708 |
| 5,164,094 A * | 11/1992 | Stuckart | ......................... | 210/708 |
| 5,711,888 A * | 1/1998 | Trampler et al. | ........ | 210/748.05 |
| 6,332,541 B1 * | 12/2001 | Coakley et al. | .................. | 209/18 |
| 2006/0246490 A1 * | 11/2006 | Anderson et al. | .................. | 435/6 |
| 2009/0226994 A1 * | 9/2009 | Lemor et al. | ................. | 435/173.1 |
| 2010/0126922 A1 * | 5/2010 | Takahashi et al. | ............. | 210/201 |
| 2010/0193407 A1 * | 8/2010 | Steinberg et al. | ............. | 209/155 |
| 2010/0323342 A1 * | 12/2010 | Gonzlez Gomez et al. | ...... | 435/5 |
| 2011/0024335 A1 * | 2/2011 | Ward et al. | .................... | 209/210 |
| 2011/0154890 A1 * | 6/2011 | Holm et al. | ................... | 73/61.75 |

FOREIGN PATENT DOCUMENTS

WO    WO 2010024753 A1 *   3/2010

* cited by examiner

*Primary Examiner* — Joseph C Rodriguez

(57) ABSTRACT

A particle sorting cell (10) comprises a cavity (12), an inlet (16) of a fluid flow (14) into the cavity, a first outlet (18) of a first part (22) of the fluid flow out from the cavity and a second outlet (20) of a second part (24) of the fluid flow out from the cavity. The second outlet is displaced from the first outlet in a first direction (Y) transverse to the flow direction (X). An acoustic generator (40) is arranged to apply an acoustic standing wave. The standing wave is transverse to the flow direction as well as to the first direction. A controller (42) is arranged to control a selective operation of the acoustic generator in dependence of an input data signal (44) associated with a particle (32) comprised in the fluid flow. The particle (32) can selectively be separated into the first outlet or the second outlet.

13 Claims, 7 Drawing Sheets

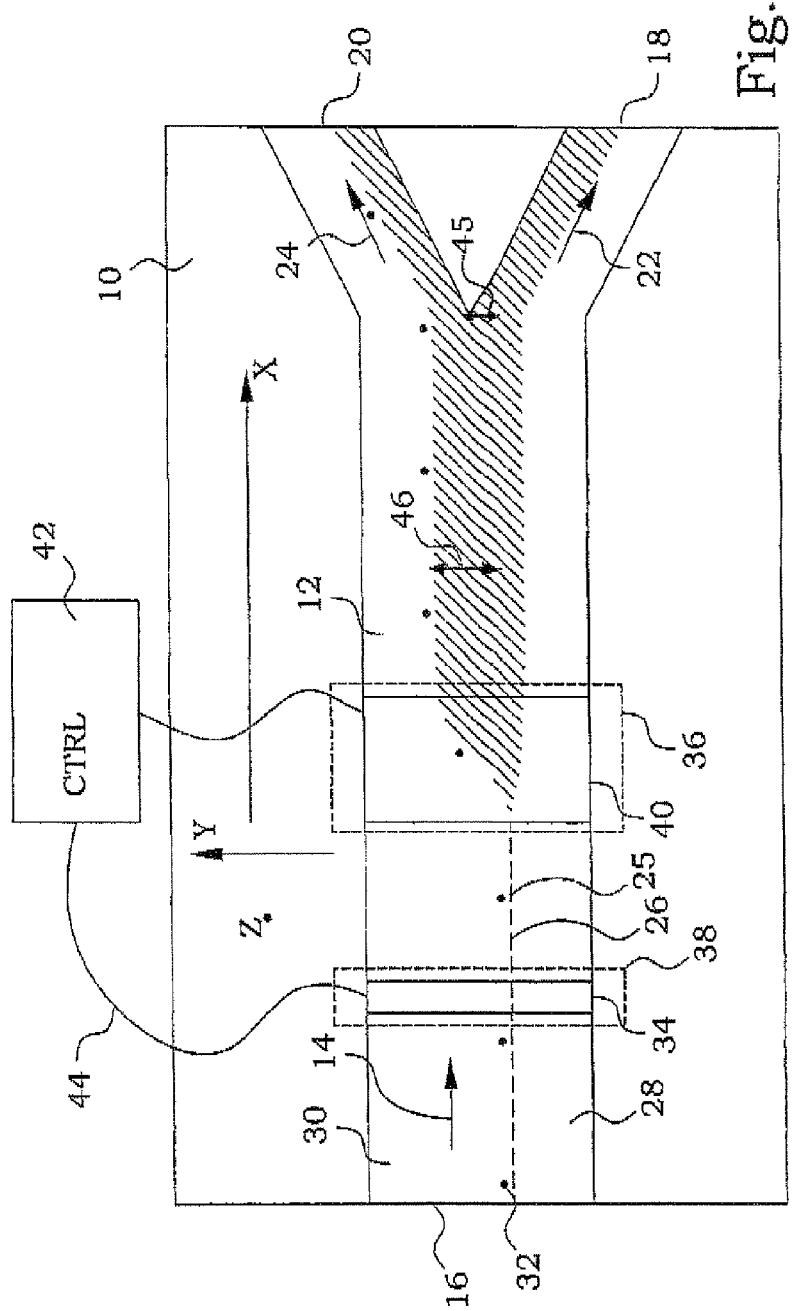
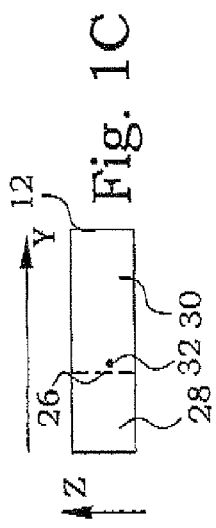

PARTICLE SORTING

TECHNICAL FIELD

The present invention relates in general to methods and devices for particle sorting and in particular to such methods and devices utilizing acoustic waves.

BACKGROUND

In many microbiological procedures, there is a need for separating different types of particles, typically cells, from each other. There are e.g. large scale fluorescence-activated cell sorters, FACS, offering cell throughputs of even up to 20000 particles per second. However, such equipment is complex, expensive and requires well-educated operators. The environment for the particles to be sorted is often also quite tough. In applications when the throughput is not the most crucial parameter, smaller, less complex and less expensive solutions would be to prefer. Such small scale solutions also enable integration with other microfluidic modules to enable several tasks in so called lab-on-a-chip solutions.

There is a number of small scale particle sorter equipments proposed, typically intended as on-chip arrangements. Some techniques rely on physical differences between the particles, so-called label-less sorting. However, since the sorting is dependent on the actual particle properties, such approaches are not generally applicable to all types of particles. One example of a label-less separation method based on acoustic forces on particles in a stationary wave is disclosed in the U.S. Pat. No. 6,929,750. In the published international patent application WO 2004/024287, an apparatus for directing particles in a fluid to a plane surface boundary is disclosed. An ultrasound standing wave with a single pressure node is utilized to move the particles towards a pressure node or anti-node along the standing wave.

A similar technique is utilized in the published U.S. patent application 2006/0163166 to separate particles that are differently responsive to such standing waves.

Another group of techniques are called labelled techniques, where the particles of interest are labelled at some stage. A typical example of such a label is a fluorescent substance selectively attached to the particles of interest. In the stream of particles, the labelling is detected and a successive sorting makes use of the detection information and some switch is used to displace the particles accordingly. The switching can be performed by different techniques, either moving the particles or the fluid which contains the particles. Non-exclusive examples are hydro-dynamical switching, optical sorting, electro-kinetic sorting and magnetic sorting.

Prior art micro-sorting methods have different disadvantages. Some of them expose the particles for incautious handling, e.g. high electrical fields, high optical intensity or heat. Other methods put severe demands on e.g. the fluids in which the particles are transported, e.g. electrokinetic methods, which make integration with other systems difficult. Further other methods involve movable puts, which may be sources for clogging.

SUMMARY

An object of the present invention is to provide devices and methods for particle sorting which are generally independent on particle properties and easily integrated with other equipment used for handling particles. The devices should also preferably be free from movable parts and be suitable for on-chip designs. Furthermore, the sorting principles should preferably be gentle to the particles to sort. Preferably, the sorting should be performed on a continuous flow of particles.

The above objects are achieved by methods and devices according to the enclosed patent claims. In general words, according to a first aspect, a particle sorting cell comprises a cavity, an inlet of a fluid flow into the cavity, a first outlet of a first part of the fluid flow out from the cavity and a second outlet of a second part of the fluid flow out from the cavity. The fluid flow has a flow direction between the inlet and the first and second outlets. The second outlet is displaced from the first outlet in a first direction transverse to the flow direction. An acoustic generator is arranged to apply an acoustic standing wave in a separation zone of the fluid flow within the cavity. The standing wave is transverse to the flow direction as well as to the first direction. The particle sorting cell further comprises a controller, arranged to control a selective operation of the acoustic generator in dependence of an input data signal associated with a particle comprised in the fluid flow. The particle can thus selectively be separated into the first outlet or the second outlet.

According to a second aspect, a particle sorting system comprises a particle sorting cell according to the first aspect. The particle sorting system further comprises a flow provider, fluidly connected to the inlet and arranged for providing a continuous laminar fluid flow into the cavity. The fluid flow has a physical property interface. The physical property interface has a normal directed perpendicular to the flow direction and transverse to the acoustic standing wave. The flow provider is further arranged for providing particles in the laminar fluid flow adjacent to the physical property interface and separated in the flow direction. A detector is arranged for detecting at least one of particle properties and numbers of particles of the fluid flow, and for supplying the controller with the input data signals in response to the detected at least one of particle properties and numbers of particles.

According to a third aspect, a method for particle sorting comprises providing of a continuous laminar fluid flow. The fluid flow has a physical property interface. The physical property interface has a normal directed perpendicular to the flow direction. The method further comprises providing of particles in the laminar fluid flow adjacent to the physical property interface and separated in said flow direction. Input data signals that are associated with a first particle of the particles are obtained. An acoustic standing wave is selectively applied, in response to the input data signals, in a separation zone of the laminar fluid flow when the first particle passes the separation zone. The acoustic standing wave is transverse to a normal of the physical property interface and transverse to the flow direction. When no acoustic standing wave is applied, the first particle is let to be separated into a first fraction. When the acoustic standing wave is applied, a displacement of a particle flow path of the first particle transverse to the flow direction into a second fraction is caused.

One advantage with the present invention is that the method is possible to apply to virtually all types of particles, since the physical forces only indirectly are applied on the particles. Thereby, the influence on the particles themselves is generally very gentle. The devices according to the invention are easily designed for on-chip purposes and at least in the most basic appearance, the devices lack movable parts. The use of a simple physical property interface, typically a density interface, put very low restrictions on which fluids that can be used, which increases the compatibility with possible other systems. The device principles are also easily realized in small sizes, which reduce the volume needed for the particle transport. The device is also suitable to operate on a continuous flow, even if also other types of flows can be handled.

Other advantages are further described in connection with different embodiments of the invention.

BRIEF DESCRIPTION OF THE DRAWINGS

The invention, together with further objects and advantages thereof, may best be understood by making reference to the following description taken together with the accompanying drawings, in which:

FIG. 1B is a schematic illustration of the particle sorting cell according to FIG. 1A, with an applied standing wave;

FIG. 1C is a cross-sectional view of the particle sorting cell according to FIG. 1A;

DETAILED DESCRIPTION

Throughout the drawings, the same reference numbers are used for similar or corresponding elements.

Figure 1A:
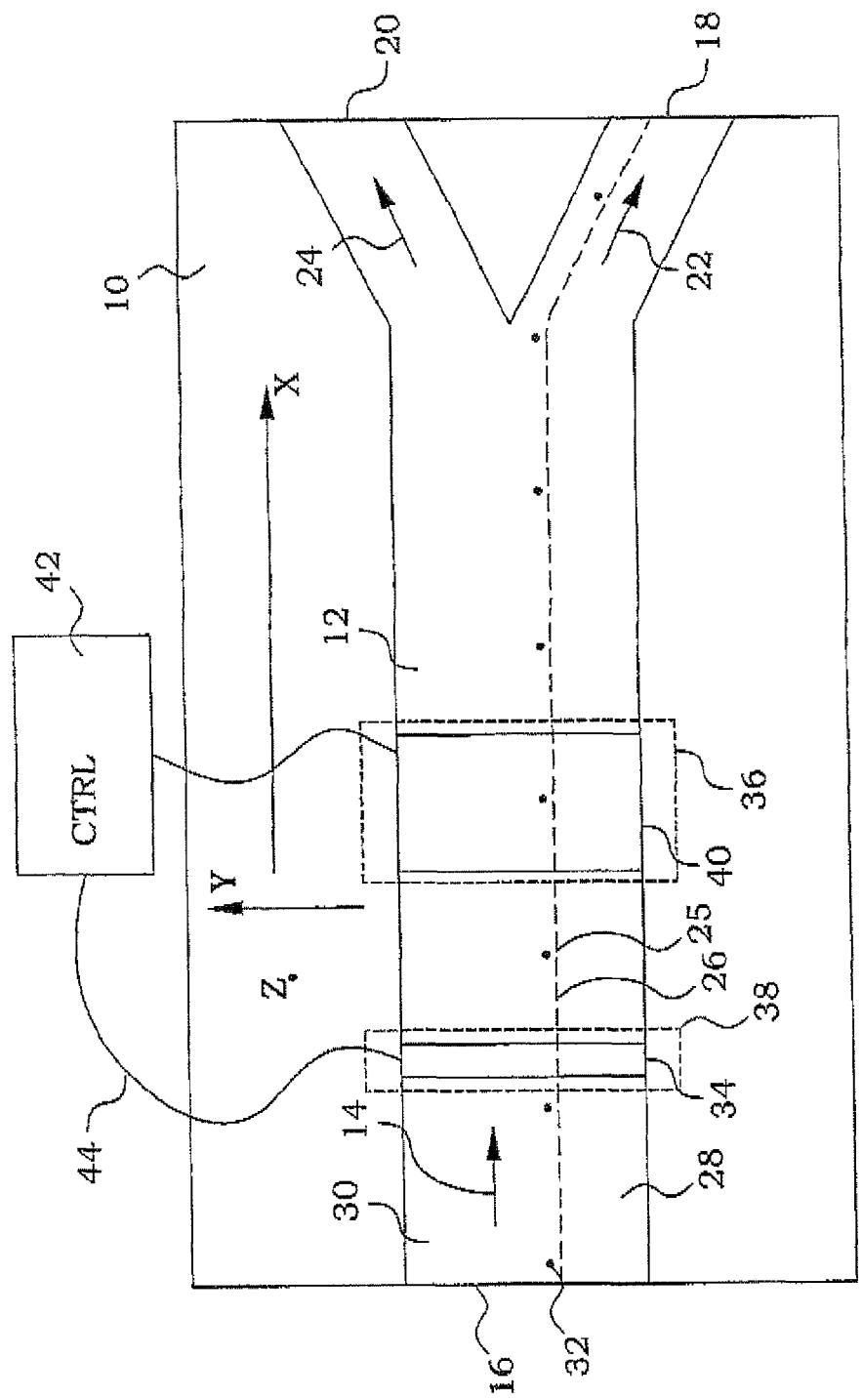
FIG. 1A is a schematic illustration of a particle sorting cell according to an embodiment of the present invention.

FIG. 1A illustrates schematically a particle sorting cell 10 according to an embodiment of the present invention. The particle sorting cell 10 comprises a cavity 12, in the present embodiment having an inlet 16, a first outlet 18 and a second outlet 20. The inlet 16 allows a fluid flow 14 to enter the cavity 12 and to flow in essentially a flow direction X between the inlet 16 and the first and second outlets 18, 20. The first and second outlets 18, 20 are displaced relative to each other in a first direction Y, perpendicular to the flow direction X. The fluid flow 14 is divided into a first and a second part flow 22 and 24, respectively, exiting through a respective outlet 18, 20.

The fluid flow 14 is provided to the inlet 16 having a physical property interface 26. A first fluid component 28 of the fluid flow 14 on one side of the physical property interface 26 thus has a physical property that differs from a second fluid component 30 of the fluid flow 14 on the opposite side of the physical property interface 26. The physical property interface 26 is in the present embodiment a density interface 27, which means that the fluids on opposite sides of the density interface 27 exhibit different densities. However, in alternative embodiments, the physical property interface 26 can be of other types, e.g. viscosity. The fluid flow 14 also comprises particles 32 to be sorted. The particles 32 are positioned adjacent to the physical property interface 26 in the fluid flow 14. The particles can be provided at either side of the physical property interface 26.

The cavity 12 has relatively small dimensions. Test equipments, having a width in the first direction Y of typically in the order of 1 mm have been used. The height dimension, i.e. the dimension perpendicular to both the first direction Y and the flow direction X, is typically even smaller. The height dimensions determine what acoustic driving frequency to be used. A smaller dimension enables a higher driving frequency with stronger acoustic radiation force as result. The small dimensions assure that a laminar flow is achieved through the cavity 12 if no additional disturbances are applied. Without any outer disturbances, the fluid flow will thus pass the cavity, keeping the physical property interface 26 at the same position in the first direction Y. In the illustrated embodiment, the physical property interface 26 and thus the particles in its vicinity will under such circumstances exit the cavity 12 in the first part flow 22 exiting the outlet 18.

A detector 34 is positioned in a detection zone 38 of the particle sorting cell 10. The detection zone covers at least a part of the cavity 12 through which the physical property interface 26 of the fluid flow 14 passes. The detector 34 is in the present embodiment arranged for detecting a particle property of the particles 32 in the fluid flow 14. The detector 34 can be provided in the wall of the cavity 12 or as an external equipment for e.g. optical detection. The particle sorting cell 10 also has also a separation zone 36. The detection zone 38 is situated upstream of the separation zone 36. An acoustic generator 40 is provided in the separation zone 36 and arranged for applying an acoustic standing wave through the fluid flow 14 in the separation zone 36, i.e. within the cavity 12. Typically, the acoustic generator is provided as a cavity wall or in acoustic contact with a cavity wall, in order to efficiently apply the acoustic waves.

A controller 42 is connected to the acoustic generator 40 and arranged to control a selective operation of the acoustic generator 40. The selective operation is made in dependence of an input signal 44, associated with a particle 32 comprised in the fluid flow 14. In the present embodiment, the input signal 44 is provided by the detector 34. Since the detector 34 is situated upstream of the separation zone 36, the operation of the acoustic generator 40 can be adapted to a time when the particle 32 in question has moved into the separation zone 36. This requires that a predetermined flow rate is maintained. Furthermore, in order to be able to treat each individual particle 32 separately within the separation zone 36, the distance between each particle 32 should be at least equal to the length of the separation zone 36 in the flow direction X.

FIG. 1B illustrates the situation where the acoustic generator 40 is operating. A standing acoustical wave is provided in the separation zone 36 in a second direction Z (directed out of the plane) perpendicular to the flow direction X and parallel to the physical property interface 26. In other words, the physical property interface 26 has a normal direction directed perpendicular to the flow direction X and the second direction Z of the standing acoustic wave. The frequency of the acoustic signal generated by the acoustic generator 40 is tuned to suit the dimensions of the cavity 12 in the Z direction, taking the speed of sound of the fluid into account. FIG. 1C illustrates the cavity 12 in cross-section upstream of the separation zone 36. The physical property interface 26 is seen as a line and where the particles 32 are situated in vicinity of the physical property interface 26.

As seen in FIG. 1B, the application of the standing acoustic wave results in a motion of the physical property interface 26. At least a part of the physical property interface 26 moves in the first direction Y a distance illustrated by the double arrow 46. The particles 32 follow motion of the fluid and are also moved in the first direction Y. The distance 46 is larger than the distance 45 between the original position of the particles 32 and the splitting point between the outlets 18, 20. This results in that the particles now instead exit from the cavity 12 in the second part flow 24 through outlet 20. In this manner a moving action on the particles 32 is achieved, which is more or less independent of the particle properties. Instead, the particles follow the motion of the fluid generated at the physical property interface 26 of the fluid flow 14.

As will be explained more in detail further below, different parts of the physical property interface 26 is displaced differently, which is illustrated in FIG. 1B as a hatched area.

Figure 1D:
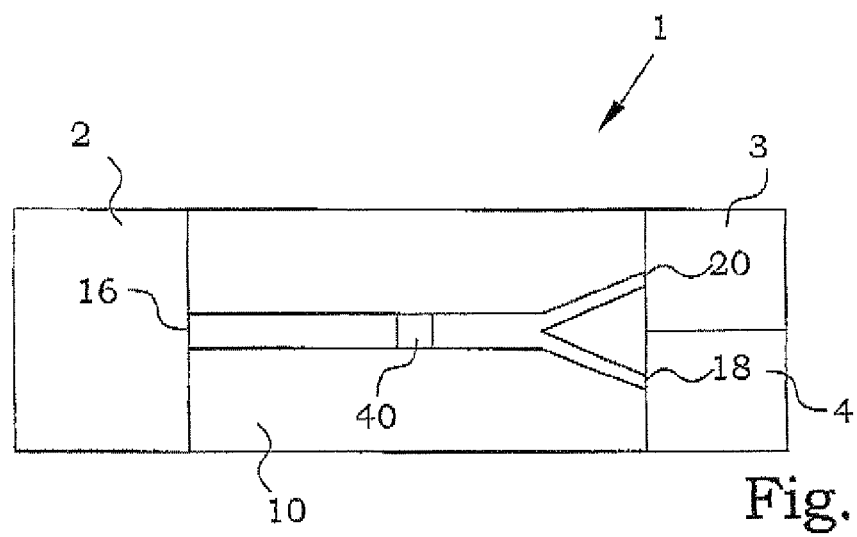
FIG. 1D is schematic illustration of a particle sorting system according to an embodiment of the present invention.

A particle sorting cell system 1 is schematically illustrated in FIG. 1D. A particle sorting cell 10 is in fluid connection by its inlet 16 to a flow provider 2. The flow provider is arranged for providing a continuous laminar fluid flow into the cavity of the particle sorting cell 10. A first fluid collector 3 and a second fluid collector 4 are fluidly connected to the outlets 18, 20 of the particle sorting cell 10. By operating the acoustic generator 40, particles following the fluid flow can be selectively sorted in either of the collectors 3, 4.

The motion of the physical property interface in the first direction Y is caused by an acoustic radiation force. Particles present in one of the fluids will move with that flow. A theoretical model for such a force is discussed for the case of density interfaces in the Appendix. A more conceptual description is given here below in connection with FIGS. 2A-D.

Figure 2A:
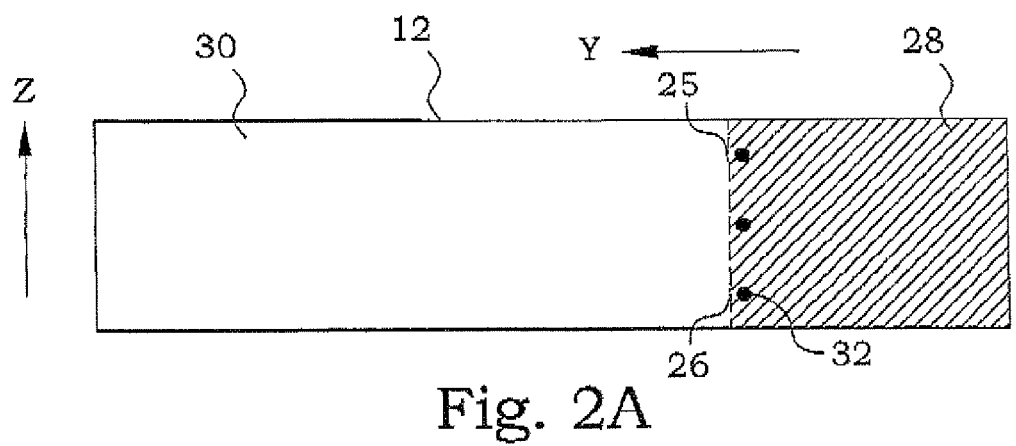
FIG. 2A-D are cross-sections of cavities of particle sorting cells illustrating the action of acoustic radiation forces.

FIG. 2A illustrates a cross-section of a cavity 12. A first fluid component 28 is separated from a second fluid component 30 by a physical property interface 26. In the discussions below, a density interface 25 is assumed. The first fluid component 28 is in this embodiment assumed to have a higher density than the second fluid component 30. Particles 32 are provided close to the density interface 25 within the first fluid component 28.

Figure 2B:
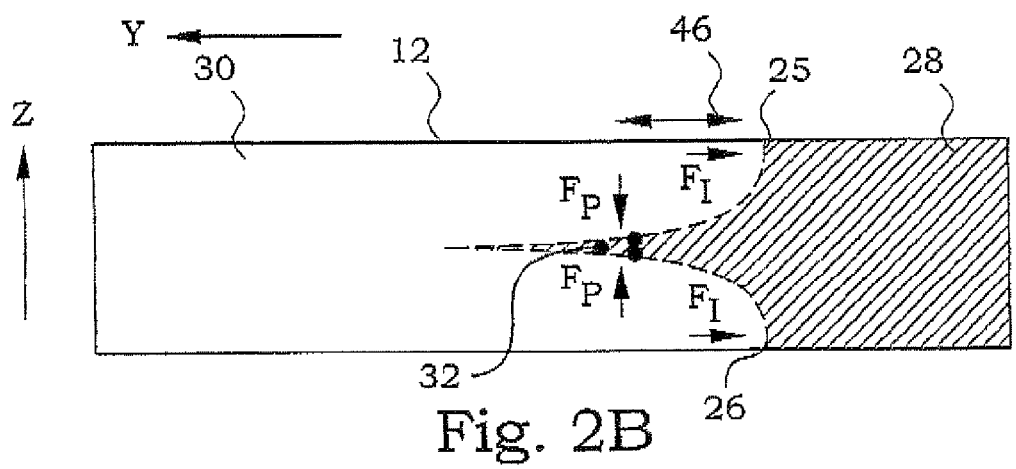

Now, consider FIG. 2B. Here, a standing acoustic wave has been applied in the second direction Z. A primary radiation force is thereby applied on the particles 32, $F_P$, tending to move the particles 32 in the second direction Z. For particles 32 having a positive acoustic contrast factor, which is the typical condition and which is assumed in the present embodiment, the primary radiation force $F_P$ is directed to the middle part of the cavity 12. The strong $F_P$ acts as a "pre-focusing effect", collecting the particles 32 in the middle of the fluid flow. Moreover, there is an acoustic radiation force $F_I$, acting, not at the particles 32 as such, but at the density interface 25. This acoustic radiation force $F_I$ is directed in the first direction Y, directed into the high density fluid component, in this embodiment the first fluid component 28. The acoustic radiation force $F_I$ is expected to be highest at the top and bottom walls of the λ/2-cavity 12 as illustrated. Due to the conservation of mass flow, a flow in the opposite direction has to occur in the middle of the fluid flow, where the particles 32 now have been pre-focused. The acoustic radiation force $F_I$ causes the density interface to be displaced towards the high-density fluid component, causing the middle part to be pushed away in the other direction, dragging the particles along with it. This means that also the particles 32 experience a displacement 46 along the first direction Y.

Figure 2C:
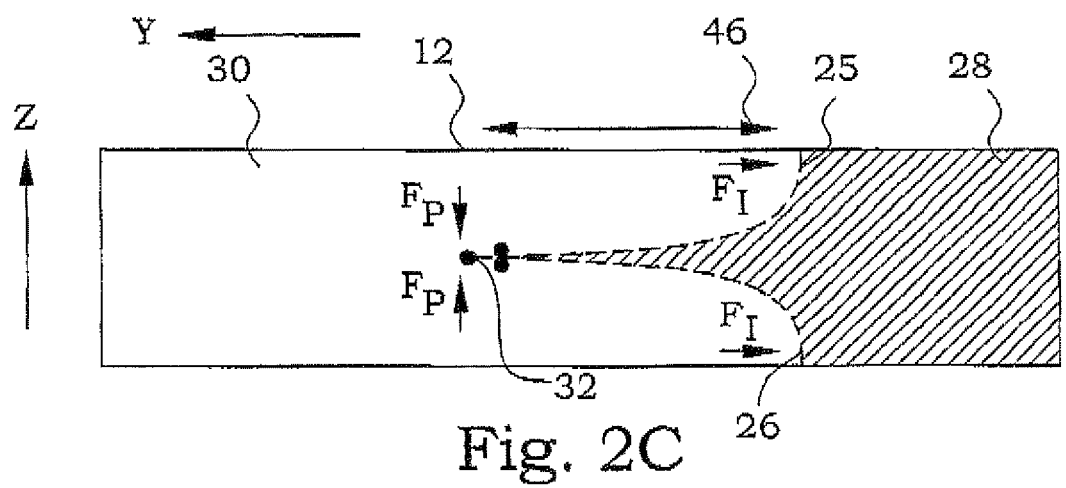

FIG. 2C illustrates another embodiment, where the particles instead are introduced into the low-density fluid component 30. One notices, that regardless of which side of the density interface 25 the particles are situated, they will follow the displacement of the density interface 25.

Figure 2D:
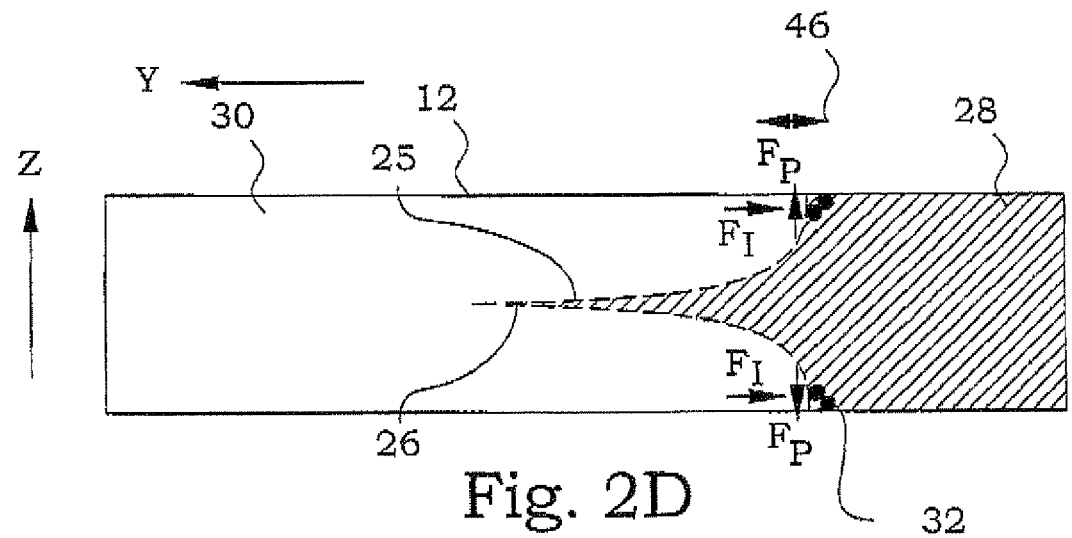

In the embodiment of FIG. 2D, the particles 32 are lipids, which possess a negative contrast factor. This in turn means that the particles 32 in this embodiment instead are pre-focused at the top and bottom of the cavity 12. They are thereby collected in the volumes affected by the positively directed acoustic radiation force $F_I$, resulting in dragging the particles 32 towards the high-density fluid component 28. A displacement 46 of the particles 32 is also here achieved, however, in an opposite direction.

The primary radiation force $F_P$ depends on several factors, e.g. the volume of the particles and the acoustic contrast factor. The effect of the pre-focusing also depends on the flow rate, since in a high flow rate, the force has less time to act on the particles and the focusing effect will thereby be less. In some systems, the pre-focusing effect may be too low to collect the particles within regions limited in the second direction Z. In such cases, there will be particles positioned along the cavity height only slightly shifted towards the optimal-$F_P$-position and the particles will thereby experience Y-displacements to different degrees, depending on the location in the second direction Z. In the extreme case of no pre-focusing and the particles distributed along the whole channel height, the Y-displacements will occur in different directions. The application of an acoustic standing wave will in such a case just spread the particles around in the Y direction and a separation is not possible to perform. In such systems, some other form of vertical positioning may be used such as for instance a chimney inlet or flow lamination by ridges in the channel structure.

Figure 3:
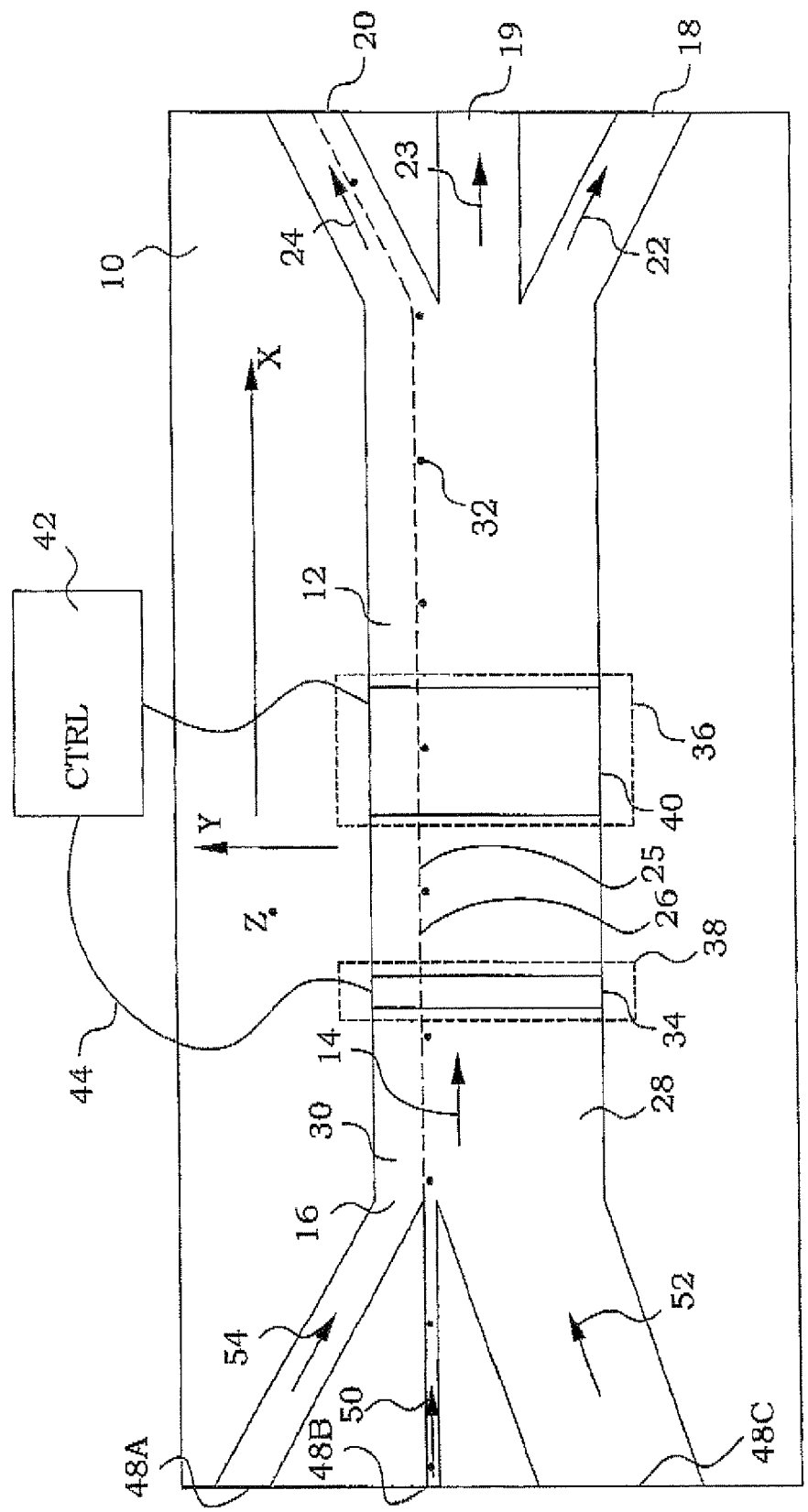
FIG. 3 is a schematic illustration of a particle sorting cell according to another embodiment of the present invention.

FIG. 3 illustrates another embodiment of a particle sorting cell 10. This particle sorting cell 10 is realized as an on-chip solution and has three part inlets 48A, 48B and 48C. A sample flow 50, comprising a fluid of a first density in which particles are distributed, is provided to the narrow middle inlet 48B. A sheath flow 52, comprising the same fluid as in the sample flow 50, but without particles is provided to the inlet 48C. A shuffle flow 54, comprising a fluid with a slightly different density as compared with the sheath flow 52 is provided to the inlet 48A. When the part inlets 48A-C merge at the inlet 16 into the actual cavity 12, the sheath flow 52, the sample flow 50 and the shuffle flow 54 merge into one single fluid flow 14, having a density interface 25.

At the opposite side of the particle sorting cell 10 of the present embodiment, three outlets 18, 19, 20 are provided. When no acoustic waves are provided into the cavity, the interface and thereby the particles 32 exit the particle sorting cell 10 in a part fluid flow 24 through the outlet 20. If an acoustic standing wave having a moderate power is applied, the density interface 25 and thereby the particles 32 are displaced a small distance in the first direction Y and exit the particle sorting cell 10 in a part fluid flow 23 through the outlet 19. When a strong acoustic standing wave is applied, a larger displacement of the interface 25 is achieved and the particles 32 will exit the particle sorting cell 10 in a part fluid flow 22 through the outlet 18. By this embodiment, the particles can thus be sorted into three different categories.

As anyone skilled in the art realizes, this can be further developed by having even more outlets, taking care of separate particle fractions as separated by applying acoustic waves of different powers and is only limited by the accuracy in displacement that can be achieved. The present ideas can thus be extended to separation of differently labelled particles. By using several labels and several outlets, simultaneous sorting of several types of particles is possible by adjusting the voltage and thereby adjusting the amount of displacement.

Another factor that influences the size of the displacement is the size of the difference in physical properties, in particular density, between the different part flows. One has observed displacements in fluid flows having only 0.5% difference in density over the density interface, but preferably the density difference should be at least 1% and even more preferably in the range of 2-5% for a fluid flow in the range of 1-25 mm/s and a channel width and height of 1 mm and 70 μm, respectively. This requirement of an interface is not difficult to obtain e.g. for a cell buffer, and cells may thus easily be dissolved in an ordinary cell buffer to be used in the sorting process.

Figure 4:
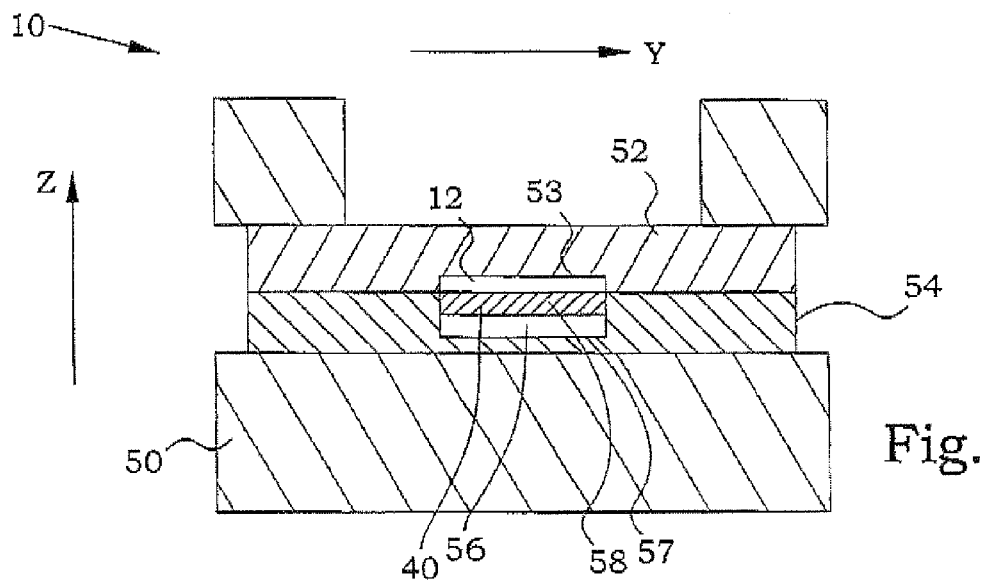
FIG. 4 is a cross-sectional view of a particle sorting cell test equipment according to yet another embodiment of the present invention.

A test equipment of a particle sorting system according to an embodiment of the present invention has been built and tested. FIG. 4 is a cross-section view of the test equipment through the separation zone. A glass plate 52 and a printed circuit board 54 are clamped together by a brass holder 50. The cavity 12 is provided as a recess 53 in the glass plate 52. The top layer of the recess 53 acts as a reflecting structure for the acoustic waves. The structure was fabricated by wet etching of borosilicate glass wafers to a reflector thickness of 1001 μm and 71 μm channel depth. The channel height determines the resonance conditions for the standing wave. A preferred range of cavity height is in the range of 10-100 μm, but both smaller and larger cavities are also possible to use. The channel size is downward limited by increasing back pressure and the size of the particles. Also, the increased acoustic absorption at high frequencies required for a standing wave in a small cavity may impose a limitation. The channel size is upward limited by maintaining the laminar flow conditions. In addition, avoiding acoustic cavitation is necessary and therefore the driving frequency should preferably be higher than 1 MHz.

The cavity enclosure preferably is of a highly acoustical reflecting material in order to enable high acoustic energy containment in the cavity. However, for lower energy containment and higher driving voltages for the transducer, other channel materials might also be used. If using glass and since glass wet etching is usually isotropic, the cavity design is not limited to specific angles relative crystallographic directions, as for instance with silicon.

A piezoceramic transducer 58 is in this embodiment provided as the acoustic generator 40. The surface of the piezoceramic transducer 58 constitutes one wall of the cavity 12 in the separation zone. The piezoelectric transducer 58 in this particular embodiment was a miniature single layer lead zirconium titanate ultrasound transducer with the measures of 900×900×200 μm³. The transducer was mounted on the 1.5 mm thick printed circuit board 54 by conducting silver paint. Epoxy was cast around the transducer and after curing, the surface was polished. Top electrodes of the transducer 58 were deposited by evaporating Au. A 5 μm thick Parylene C coating was added in order to protect the metal surface during channel re-assembly and also to prevent contact between the sample and the epoxy. The coating step improved the biocompatibility of the device since both glass and Parylene C can be considered as inert materials.

Due to the relatively small transducer area, the action is located to a small part of the cavity, the separation zone. For this small excitation area and by having the transducer in direct contact with the fluid, there is minimal risk of supporting an acoustic standing wave in other parts of the cavity.

The transducer is in the present embodiment a piezoelectric transducer based on PZT material defined by thick film processing. Another alternative is SAW (Surface Acoustic Waves) such as AlN, piezoelectric polymer or composite transducers. Other ways of introducing the motion may also be used such as electrostatic deflection or membrane motion. The transducer may be integrated or external. In the present embodiment, the transducer is integrated in the bottom channel wall. Several transducers may also be used. If the transducers are positioned in series, the displacement response may be increased.

In order to ensure high reflectance at the transducer back side, a recess 57 is also provided in the printed circuit board 54, thereby giving rise to an air volume 56.

Figure 5:
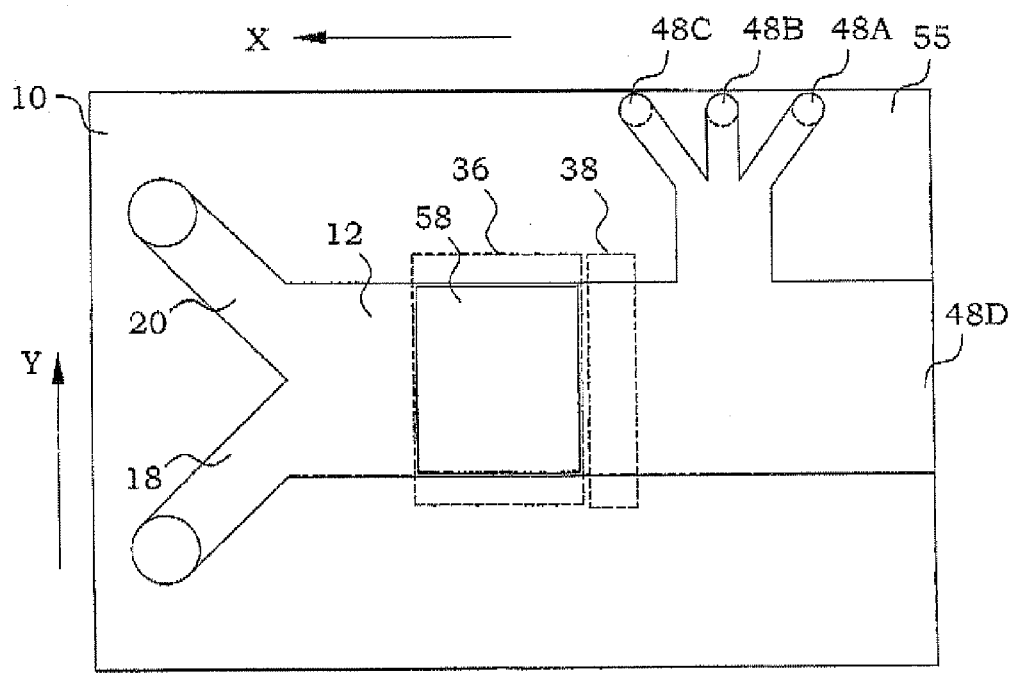
FIG. 5 is another cross-sectional view of the particle sorting cell test equipment of FIG. 4.

A cross-sectional view of the test equipment of FIG. 4 is illustrated in FIG. 5. Here four part inlets 48A-D are shown. Part inlet 48C is a shuffle flow inlet, part inlet 48B is a sample flow inlet and part inlet 48A is a sheath flow inlet, all being supplied through the glass plate 52, as indicated by the dashed holes. Part inlet 48D is an additional sheath flow inlet provided in the plane of the cavity 12. The amount of shuffle fluid was in the experiments varied between 2 and 5 times the amount of sample fluid. The amount of fluid in each of the sheath flows were 10 times the amount of sample fluid. The outlets 18 and 20 are also exiting in a direction perpendicular to the illustration, though the PCB 54. Inlets 48A-D and outlets 18 and 20 can be supplied from eligible sides, i.e. through the glass plate 52 or the PCB 54.

During the experiments, a solution of 17% glycerol in deionised water was used as shuffle fluid and sample fluid. The sheath fluids consisted of deionised water. A syringe pump was used to drive the flows. A total volume flow in the cavity of 6.9-104.0 μL/min was used during the evaluation, corresponding to a Reynolds number of 0.2-3.

For a first evaluation, the particles were 9.9 μm and 1.9 μm co-polymeric particles dissolved in 17% glycerol in deionised water. The particles emit green fluorescence and can easily be detected. The detector used in these experiments was an inverted microscope with a high sensitive cooled CCD camera. For investigating particles with negative contrast factor, a sample flow of lipids in water was also studied. Biological cells were also tested. Syto13-labeled rat neuron cells with a diameter of 10-15 μm were used.

Fluorescently labelled incoming particles or cells were detected in the detection zone and automatic switching was performed by supplying the transducer with a sinusoidal signal with a delay time corresponding to the time required for the cell to reach the transducer. A cell was identified when the intensity within the detection zone exceeded a threshold value. During the experiments, approximately five images were processed per second. The automatic switching was evaluated by analysing particles in the outlets.

The transducer was excited by a high-frequency generator and an in-house manufactured amplifier. The voltage at the transducer was 8V peak-to-peak. This excitation signal was decreased at low flow velocities in order to avoid acoustic trapping of the cells. The optimal driving frequency in the present embodiment was identified to be 10.3 MHz. From an acoustic point of view, in order to avoid acoustic cavitation, the driving frequency should preferably be higher than 1 MHz.

The separation ability was confirmed. For instance, the displacement of the trajectory of the 9.9 μm particles was measured to be up to 730 μm relative an undisturbed trajectory. As described above, the trajectory follows the displacement of the density interface.

The exit position of the particles was evaluated for increasing fluid velocity. The maximum theoretical speed can be assumed to be close to the assumption that a sample concentration is used which allows one particle to be placed above the transducer at the same time. For a given flow velocity resulting in 27 particles per second the particle displacement was 220 μm and for a corresponding flow of 2 particles per second the particle displacement was 650 μm.

The residence time, i.e. the time a defined fluid volume is located above the transducer influenced the level of displacement. A lower level of displacement was observed for higher flow velocities. Saturation in displacement was observed at low velocities. The level of displacement is also observed to depend on the entrance position relative the transducer surface, i.e. in the second direction Z.

Figure 6:
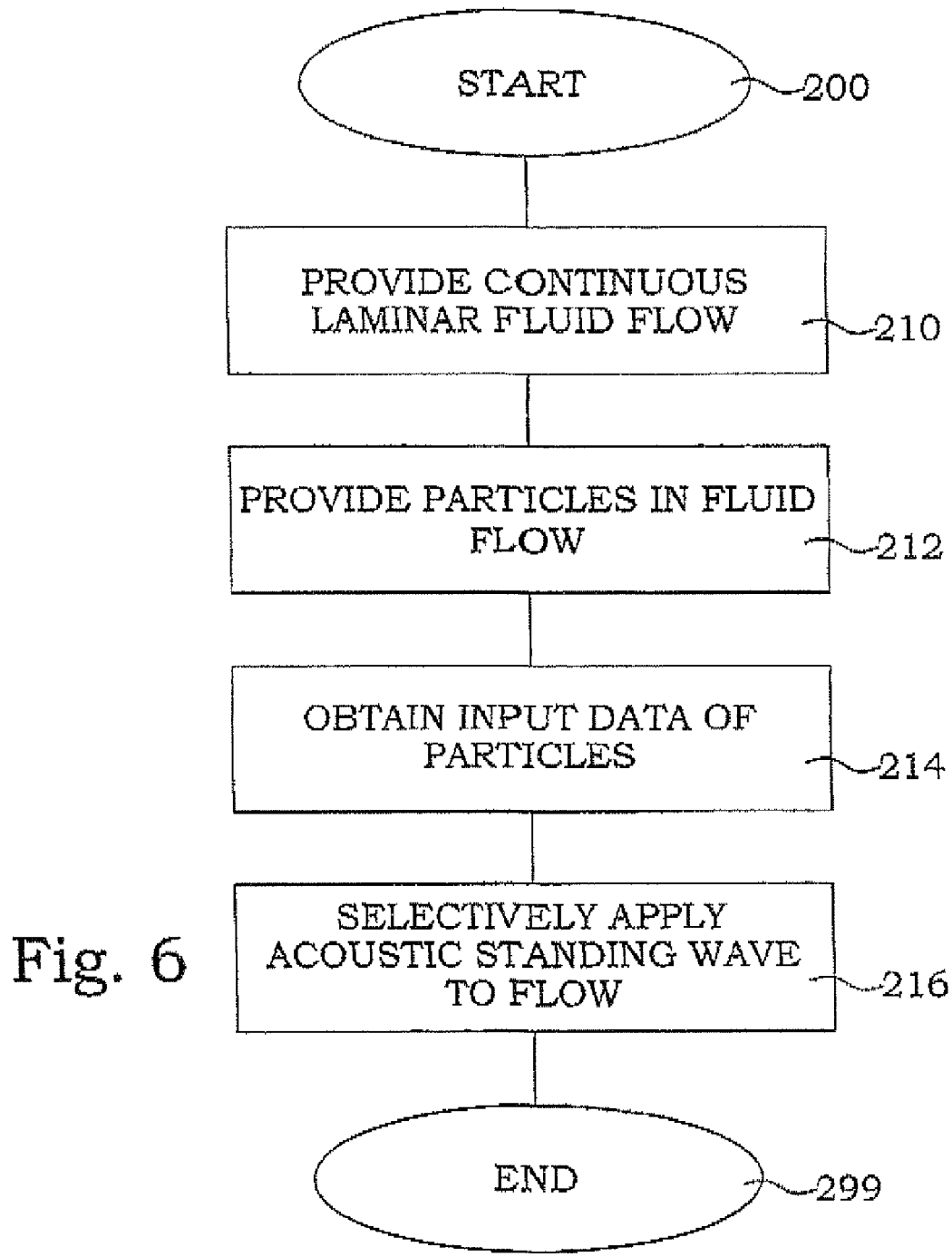
FIG. 6 is a flow diagram illustrating steps of a method according to an embodiment of the present invention.

FIG. 6 illustrates a flow diagram of steps of a method according to an embodiment of the present invention. The method for particle sorting starts at step 200. In step 210, a continuous laminar fluid flow is provided. The fluid flow has a physical property interface. The physical property interface has a normal direction directed perpendicular to a flow direction. In step 212, particles are provided in the laminar fluid flow adjacent to the physical property interface. The particles are also separated in the flow direction. Input data signal associated with a certain particle is obtained in step 214. In step 216, an acoustic standing wave is selectively applied in a separation zone of the laminar fluid flow in response to the input data signals. The application is adjusted to occur when the particle in question passes the separation zone. The normal of the physical property interface is transverse to the acoustic standing wave and to the flow direction. When no acoustic standing wave is applied, the particle in question is let to be separated into a first fraction. When the acoustic standing wave is applied, a displacement of a particle flow path of the particle in question transverse to the flow direction into a second fraction. The procedure ends in step 299.

The present invention is well suited for being combined with labelled sorting of particles. It may also be used for particles with inherent signal response such as auto-fluorescence or chemiluminescence. If the particles themselves do not have easily detectable properties, the particles have to be labelled in some way to facilitate the sorting. Labelling with e.g. fluorescent species is commonly used in biological applications and can with advantage be used also in connection with the present invention. Also other labelling techniques can be used, such as coloured dyes. Beads or other kinds of material science samples can also be coated to bind selectively to a small particle, which then is visible to detect. A sandwich ELISA concept may also be used. The actual sorting does not primarily depend on the particle properties itself, but only to the input data signal provided to the control unit for the acoustic generator.

The present invention can also be used for counting of particles. If the detector is arranged for detecting the presence of a particle, the detector may also count the number of detected particles that passes the detector. The input data signal to the control unit of the acoustic generator may thereby be supported by the number of particles that has passed the detector. This technique can also be used for separating a certain number of particles into different fractions, e.g. as a part of sample preparation. If e.g. samples having exactly 1000 particles are requested, the detector may count the number of passing particles, and when particle 1001 is detected, the acoustic generator is activated, to displace this and following particles away from the earlier used outlet.

The general applicability to different kinds of particles makes the present invention very useful in many different applications. The displacement of the particles is due to the fluidic motions originating from the acoustic radiation forces acting on the fluid interface surface between fluids having different physical properties. Large displacements of particles can be achieved. Furthermore, since the displacement direction is perpendicular to the standing wave direction, the maximum displacement is not limited by the distance between the acoustic node and anti-node in the standing wave, which is in the range of a quarter of the wavelength in the fluid. This limits many other acoustic separation techniques. The particles can e.g. be cells or any other biosamples or beads.

The physical property interface is in most embodiments described above positioned with its normal direction essentially perpendicular to the normal direction of the acoustic generator surface, i.e. typically the cavity surface. Acoustic radiation forces may also be expected in the case of the physical property interface not seal being parallel to the generator surface normal. These two cases are the two extremes and intermediate angles may be expected to have a contribution of each of the above terms. However, the relative build-up of the acoustic energy between the two fluids may be different for such an embodiment.

The present invention enables individual handling of e.g. cells or other particles for a reasonable concentration due to the preferred miniaturized area of the acoustic generator. A device according to these principles can easily be integrated with other steps in handling different types of particles, in order to e.g. perform several operations on a single chip. Compared to larger size FACS, devices according to the present invention can be provided at much lower prices, does need less skilled operators, and is much less bulky. When compared to other micro-FACS solutions, the present method is gentle relative separation methods based on high electric fields. The integration with other needed outer instrumentation is simple. Furthermore, there are no moving parts at all.

The present invention has many fields of application. It can e.g. be used for sorting live cells from dead. In applications concerning cell-transplants, the gentle handling is appreciated. The method can also easily be used for sorting recombinant cells for production of proteins from other cells. It is possible to select stem cells from ordinary cells in e.g. bone marrow or CSF (Cerebro Spinal Fluid). The stem cells only constitute a small percentage of the total number and can easily be separated efficiently by the here presented devices.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

APPENDIX

Upon activation of an ultrasonic field, fluids are subjected to an acoustic radiation force at fluid-fluid interfaces that will cause convective motion of the fluids. A density difference in the range of a few percent is enough at the interface, between e.g. a shuffle flow and a sample flow to generate effective fluid motion. The acoustic radiation force acting on a fluid interface, $F_I$:

$$F_I(y) = i \cdot A_{interface} Q_{SW} \frac{\langle |v_i^2| \rangle}{2} \cos^2\left(\frac{2\pi}{\lambda/2}z\right)\left(\rho_{01} - \frac{Q_2}{Q_{SW}}\rho_{02}\right), \quad (1)$$

will cause a movement of the fluids perpendicular to the fluid interface, in our case in the Y direction. $\lambda$ is the wavelength of the acoustic wave, $v_i$ is the particle velocity amplitude at the acoustic generator surface, $\rho_{01}$ and $\rho_{02}$ are the densities of the first fluid component and the second fluid component, respectively, in the absence of sound. $Q_{SW}$ is the Q-factor for the first fluid component and $Q_2$ is the Q-factor for the second fluid component.

The above expression assumes stepwise density difference at the density interface and the force will be reduced as the density difference decreases clue to any convective motions caused by the radiation force. The viscous forces have been omitted for simplicity but will act to reduce the effect and increases with fluid motion.

A particle in the fluid is expected to be displaced in the channel as a result of the fluid motion in the channel according to the Stokes drag force, $F_S$:

$$F_S(y) = 6\pi\eta r v_y^F, \qquad (2)$$

for a movement of the fluid in the first direction with velocity $v_y^F$ due to the acoustic radiation forces at the fluid interface. $\eta$ is the viscosity of the fluid and r is the radius of a spherical particle. All particles or cells with similar volume are expected to be displaced to the same amount. Stokes drag force acts upon the particles that have a velocity different than their surrounding medium. Additional effects, e.g. gravity force and momentum from the initial forward fluid motion may also affect the particle trajectory. However, unless the particles are very heavy and small, the particles will take the trajectory of the medium in which they are dissolved.

In addition, the primary radiation forces on the particles will cause a pre-alignment in the second direction Z. The primary radiation force on a particle, $F_P$, may be expressed as:

$$F_P(z) = \frac{4\pi r^3}{3} f p_o^2 \left(\frac{\pi}{2\rho_0 c_0^3}\right)\left(f_1 + \frac{3}{2}f_2\right)\sin\left(\frac{2\pi}{\lambda/2}z\right) \qquad (3)$$

where r is the radius of the particle, $p_a$ is the sound induced pressure amplitude, $\rho_o$ is the density of the fluid, $c_0$ is the speed of sound of the fluid and $f_1$ and $f_2$ are defined as:

$$f_1 = 1 - \frac{\rho_0 c_0^2}{\rho c^2} \qquad (4)$$

and $$f_2 = \frac{2(\rho - \rho_0)}{2\rho + \rho_0}. \qquad (5)$$

where $\rho$ is the density of the particle and c is the speed of sound of the particle. The parenthesis containing the $f_1$ and $f_2$ is referred to as the acoustic contrast factor.

The invention claimed is:

1. A particle sorting system, comprising:
    a particle sorting cell, in turn comprising:
        a cavity;
        an inlet of a fluid flow into said cavity;
        a first outlet of a first part of said fluid flow out from said cavity;
        a second outlet of a second part of said fluid flow out from said cavity;
        whereby said fluid flow has a flow direction between said inlet and said first and second outlets;
        said second outlet being displaced from said first outlet in a first direction transverse to said flow direction;
        an acoustic generator, arranged to apply an acoustic standing wave in a separation zone of said fluid flow within said cavity;
        said standing wave being transverse to said flow direction as well as to said first direction; and
        a controller, arranged to control a selective operation of said acoustic generator in dependence of an input data signal associated with a particle comprised in said fluid flow,
        whereby said particle selectively can be separated into said first outlet or said second outlet;
    a flow provider, fluidly connected to said inlet and arranged for providing a continuous laminar fluid flow into said cavity;
    said fluid flow having a physical property interface, said physical property interface having a normal directed perpendicular to a flow direction and essentially perpendicular to said acoustic standing wave;
    said flow provider being further arranged for providing particles in said laminar fluid flow adjacent to said physical property interface and separated in said flow direction;
    a detector arranged for detecting at least one of particle properties and numbers of particles of said fluid flow, and for supplying said controller with said input data signals in response to said detected at least one of particle properties and numbers of particles.

2. The particle sorting system of claim 1, wherein said detector is positioned upstream of said separation zone and said controller is arranged for applying said acoustic standing wave when a particle, to which said input data signals is associated, passes said separation zone, if said detector has detected a certain property or said first particle is within a certain number interval.

3. The particle sorting system of claim 2, wherein said physical property interface is a density interface.

4. The particle sorting system of claim 3, wherein densities on different sides of said density interface differ by more than 0.5%.

5. The particle sorting system of claim 1, wherein said acoustic generator comprises a piezoelectric transducer arranged in a wall of said cavity.

6. The particle sorting system of claim 1, wherein said cavity has cross-sectional dimensions small enough to ensure laminar flow.

7. The particle sorting system of claim 1, wherein said acoustic standing wave has a frequency of above 1 MHz.

8. A Method for particle sorting, comprising the steps of:
    providing a continuous laminar fluid flow;
    said fluid flow having a physical property interface, said physical property interface having a normal directed perpendicular to a flow direction;
    providing particles in said laminar fluid flow adjacent to said physical property interface and separated in said flow direction;
    obtaining input data signals being associated with a first particle of said particles;
    selectively applying, in response to said input data signals, an acoustic standing wave in a separation zone of said laminar fluid flow when said first particle passes said separation zone;
    said acoustic standing wave being transverse to a normal of said physical property interface and perpendicular to said flow direction;
    when no said acoustic standing wave being applied, letting said first particle be separated into a first fraction;
    when said acoustic standing wave being applied, causing a displacement of a particle flow path of said first particle transverse to said flow direction into a second fraction.

9. The method of claim 8, wherein said particle is selected from the list of:
    a bead,
    a biosample, and
    a cell.

10. The method of claim 8, wherein said input data signals are associated with at least one of particle properties and numbers of particles.

11. The method of claim 10, wherein said applying of an acoustic standing wave is performed when a certain particle property is detected.

12. The method of claim 10, wherein said applying of an acoustic standing wave is performed when a certain number of particles have passed said detector.

13. The method of claim 8, wherein said physical property interface is a density interface.

* * * * *